United States Patent [19]

Huston et al.

[11] Patent Number: 5,525,491
[45] Date of Patent: Jun. 11, 1996

[54] SERINE-RICH PEPTIDE LINKERS

[75] Inventors: James S. Huston, Chestnut Hill; Hermann Oppermann, Medway; Serge N. Timasheff, Wellesley Hills, all of Mass.

[73] Assignee: Creative BioMolecules, Inc., Hookinton, Mass.

[21] Appl. No.: 257,341

[22] Filed: Jun. 9, 1994

Related U.S. Application Data

[63] Continuation of Ser. No. 842,149, filed as PCT/US92/01478, Feb. 27, 1992, abandoned, which is a continuation-in-part of Ser. No. 662,226, Feb. 27, 1991, abandoned.

[51] Int. Cl.$^6$ ............................. C07K 16/46; C12N 15/62
[52] U.S. Cl. .................. 435/69.7; 435/252.3; 435/320.1; 530/350; 530/387.3; 536/23.4
[58] Field of Search ..................... 435/69.7, 252.3, 435/320.1; 530/350, 387.3; 536/23.4

[56] References Cited

U.S. PATENT DOCUMENTS

| | | | |
|---|---|---|---|
| 4,769,326 | 9/1988 | Rutter | 435/69.7 |
| 4,888,280 | 12/1989 | Palmer et al. | 435/69.7 |
| 4,962,028 | 10/1990 | Bedbrook et al. | |
| 4,987,070 | 1/1991 | Magota et al. | 435/69.7 |
| 5,028,423 | 7/1991 | Prickett | 424/85.8 |
| 5,073,627 | 12/1991 | Curtis et al. | 530/351 |
| 5,095,096 | 3/1992 | Miki et al. | 530/350 |

FOREIGN PATENT DOCUMENTS

| | | |
|---|---|---|
| 0269455 | 11/1987 | European Pat. Off. . |
| 0467839 | 7/1991 | European Pat. Off. . |
| 9015860 | 6/1990 | WIPO . |
| 9104329 | 8/1990 | WIPO . |
| 9112328 | 2/1991 | WIPO . |
| 9119739 | 6/1991 | WIPO . |

OTHER PUBLICATIONS

Harrison et al, The Embo Journal 9(1) 207–216, Jan. 1940.
P.N.A.S. 85:5879–7883 (Aug. 1988) Huston et al. Protese Engineering of Antibody Binding Sites: Recovery of Specific Activity in an Anti–Digoxin Single– Chain Fr . . .
Hardbook of Brochemistry (1984) Herbert A. Sobe–Ed pp. C–68 to C–70.
Patrick Argos; J. Mol. Biol. (1990) 211:943–958.
Chaudhary et al., 1989, Nature 339;394.

*Primary Examiner*—John Ulm
*Attorney, Agent, or Firm*—Testa, Hurwitz & Thibeault

[57] ABSTRACT

Disclosed are serine-rich peptide linkers for linking two or more protein domains to form a fused protein. The peptide linkers contains at least 40% serine residues and preferably have the formula (Ser, Ser,Ser,Ser,Gly)$_y$, where y is $\geq 1$. The resulting fused domains are biologically active together or individually, have improved solubility in physiological media, and improved resistance to proteolysis.

19 Claims, No Drawings

SERINE-RICH PEPTIDE LINKERS

This application is a continuation of application Ser. No. 07/842,149, filed as PCT/US92/01478, Feb. 27, 1992 now abandoned, which is a continuation in part of application Ser. No. 07/662,226, filed Feb. 7, 1991, also abandoned.

FIELD OF THE INVENTION

The present invention is in the fields of peptide linkers, fusion proteins and single-chain antibodies.

BACKGROUND OF THE INVENTION

Two or more polypeptides may be connected to form a fusion protein. This is accomplished most readily by fusing the parent genes that encode the proteins of interest. Production of fusion proteins that recover the functional activities of the parent proteins may be facilitated by connecting genes with a bridging DNA segment encoding a peptide linker that is spliced between the polypeptides connected in tandem. The present invention addresses a novel class of linkers that confer unexpected and desirable qualities on the fusion protein products.

An example of one variety of such fusion proteins is an antibody binding site protein also known as a single-chain Fv (sFv) which incorporates the complete antibody binding site in a single polypeptide chain. Antibody binding site proteins can be produced by connecting the heavy chain variable region ($V_H$) of an antibody to the light chain variable region ($V_L$) by means of a peptide linker. See, PCT International Publication No. WO 88/09344 the teachings of which are hereby incorporated herein by reference. Suck sFv proteins have been produced to date that faithfully reproduce the binding affinities and specificities of the parent monoclonal antibody. However, there have been some drawbacks associated with them, namely, that some sFv fusion proteins have tended to exhibit low solubility in physiologically acceptable media. For example, the anti-digoxin 26–10 sFv protein, which binds to the cardiac glycoside digoxin, can be refolded in 0.01M NaOAc buffer, pH 5.5, to which urea is added to a final concentration of 0.25M to produce approximately 22% active anti-digoxin sFv protein. The anti-digoxin sFv is inactive as a pure protein in phosphate buffered saline (PBS) which is a standard buffer that approximates the ionic strength and neutral pH conditions of human serum. In order to retain digoxin binding activity in PBS the 26–10 sFv must be stored in 0.01M sodium acetate, pH 5.5, 0.25M urea diluted to nanomolar concentrations in PBS containing 1% horse serum or 0.1% gelatin, a concentration which is too low for most therapeutic or pharmaceutical use.

Therefore, it is an object of the invention to design and prepare fusion proteins which are 1) soluble at high concentrations in physiological media, and 2) resistant to proteolytic degradation.

SUMMARY OF THE INVENTION

The present invention relates to a peptide linker comprising a large proportion of serine residues which, when used to connect two polypeptide domains, produces a fusion protein which has increased solubility in aqueous media and improved resistance to proteolysis. In one aspect, the invention provides a family of biosynthetic proteins comprising first and second protein domains which are biologically active individually or act together to effect biological activity, wherein the domains are connected by a peptide linker comprising the sequence (X, X, X, X, Gly)$_y$ wherein y typically is 2 or greater, up to two Xs in each unit are Thr, and the remaining Xs in each unit are Ser. Preferably, the linker takes the form (Ser, Ser, Ser, Ser, Gly)$_y$ where Y is greater than 1. The linker preferably comprises at least 75 percent serine residues.

The linker can be used to prepare single chain binding site proteins wherein one of the protein domains attached to the linker comprises or mimicks the structure of an antibody heavy chain variable region and the other domain comprises or mimicks the structure of an antibody light chain variable domain. A radioactive isotope advantageously may be attached to such structures to produce a family of imaging agents having high specificity for target structure dictated by the particular affinity and specificity of the single chain binding site. Alternatively, the linker may be used to connect a polypeptide ligand and a polypeptide effector. For example, a ligand can be a protein capable of binding to a receptor or adhesion molecule on a cell in vivo, and the effector a protein capable of affecting the metabolism of the cell. Examples of such constructs include those wherein the ligand is itself a single chain immunoglobulin binding site or some other form of binding protein or antibody fragment, and the effector is, for example, a toxin.

Preferred linkers for sFv comprise between 8 and 40 amino acids, more preferably 10–15, most preferably 13, wherein at least 40%, and preferably 50% are serine. Glycine is a preferred amino acid for remaining residues; threonine may also be used; and preferably, charged residues are avoided.

Fusion proteins containing the serine-rich peptide linker are also the subject of the present invention, as are DNAs encoding the proteins, cells expressing them, and method of making them.

The serine-rich peptide linkers of the present invention can be used to connect the subunit polypeptides of a biologically active protein, that is, linking one polypeptide domain with another polypeptide domain, thereby forming a biologically active fusion protein; or to fuse one biologically active polypeptide to another biologically active peptide, thereby forming a bifunctional fusion protein expressing both biological activities. A particularly effective linker for forming this protein contains the following amino acid sequence (sequence ID No. 1):

-Ser-Gly-Ser-Ser-Ser-Ser-Gly-Ser-Ser-Ser-Ser-Gly-Ser-.

The serine-rich linkers of the present invention produce proteins which are biologically active and which remain in solution at a physiologically acceptable pH and ionic strength at much higher concentrations than would have been predicted from experience. The serine-rich peptide linkers of the present invention often can provide significant improvements in refolding properties of the fusion protein expressed in procaryotes. The present serine-rich linkers are resistant to proteolysis, thus fusion proteins which are relatively stable in vivo can be made using the present linker and method. In particular, use of the linkers of the present invention to fuse domains mimicking $V_H$ and $V_L$ from monoclonal antibody results in single chain binding site proteins which dissolve in physiological media, retain their activity at high concentrations, and resist lysis by endogenous proteases.

DETAILED DESCRIPTION OF THE INVENTION

The serine-rich peptide linkers of the present invention are used to link through peptide bonded structure two or more polypeptide domains. The polypeptide domains individually may be biologically active proteins or active polypeptide segments, for example, in which case a multifunctional protein is produced. Alternatively, the two domains may interact cooperatively to effect the biological function. The resulting protein containing the linker(s) is referred to herein as a fusion protein.

The preferred length of a serine-rich peptide of the present invention depends upon the nature of the protein domains to be connected. The linker must be of sufficient length to allow proper folding of the resulting fusion protein. The length required can be estimated as follows:

1. Single-Chain Fv (sFv). For a single chain antibody binding site comprising mimicks of the light and heavy chain variable regions of an antibody protein (hereinafter, sFv), the linker preferably should be able to span the 3.5 nanometer (nm) distance between its points of covalent attachment between the C-terminus of one and the N-terminus of the other V domain without distortion of the native Fv conformation. Given the 0.38 nm distance between adjacent peptide bonds, a preferred linker should be at least about 10 residues in length. Most preferably, a 13–15 amino acid residue linker is used in order to avoid conformational strain from an overly short connection, while avoiding steric interference with the combining site from an excessively long peptide.

2. Connecting domains in a dimeric or multimeric protein for which a 3-dimensional conformation is known. Given a 3-dimensional structure of the protein of interest, the minimum surface distance between the chain termini to be bridged, d (in nanometers), should be determined, and then the approximate number of residues in the linker, n, is calculated by dividing d by 0.38 nm (the peptide unit length). A preferred length should be defined ultimately by empirically testing linkers of different sizes, but the calculated value provides a good first approximation.

3. Connecting domains in a dimeric or multimeric protein for which no 3-dimensional conformation is known. In the absence of information regarding the protein's 3-dimensional structure, the appropriate linker length can be determined operationally by testing a series of linkers (e.g., 5, 10, 15, 20, or 40 amino acid residues) in order to find the range of usable linker sizes. Fine adjustment to the linker length then can be made by comparing a series of single-chain proteins (e.g., if the usable n values were initially 15 and 20, one might test 14, 15, 16, 17, 18, 19, 20, and 21) to see which fusion protein has the highest specific activity.

4. Connection of independent domains (i.e., independently functional proteins or polypeptides) or elements of secondary structure (alpha or beta strands). For optimal utility, this application requires empirically testing serine-rich linkers of differing lengths to determine what works well. In general, a preferred linker length will be the smallest compatible with full recovery of the native functions and structures of interest. Linkers wherein $1 \leq y \leq 4$ work well in many instances.

After the ideal length of the peptide linker is determined, the percentage of serine residues present in the linker can be optimized. As was stated above, preferably at least 75% of a peptide linker of the present invention is serine residues. The currently preferred linker is $(SerSerSerSerGly)_y$ [residues 3–7 of sequence ID No. 1] where y comprises an integer from 1 to 5. Additional residues may extend C-terminal or N-terminal of the linker; preferably such additional residues comprising Ser, Thr, or Gly. Up to two of each of the serine residues on each segment may be replaced by Thr, but this has the tendency to decrease the water solubility of the fusion constructs. For constructs wherein the two linked domains cooperate to effect a single biological function, such as an sFv, it is preferred to avoid use of charged residues. Generally, in linkers of more than 10 residues long, any naturally occurring amino acid may be used once, possibly twice, without unduly degrading the properties of the linker.

The serine-rich peptide linker can be used to connect a protein or polypeptide domain with a biologically active peptide, or one biologically active peptide to another to produce a fusion protein having increased solubility, improved folding properties and greater resistance to proteolysis in comparison to fusion proteins using non-serine rich linkers. The linker can be used to make a functional fusion protein from two unrelated proteins that retain the activities of both proteins. For example, a polypeptide toxin can be fused by means of a linker to an antibody, antibody fragment, sFv or peptide ligand capable of binding to a specific receptor to form a fusion protein which binds to the receptor on the cell and kills the cell.

Fusion protein according to the present invention can be produced by amino acid synthesis, if the amino acid sequence is known, or preferably by art-recognized cloning techniques. For example, an oligonucleotide encoding the serine-rich linker is ligated between the genes encoding the domains of interest to form one fused gene encoding the entire single-chain protein. The 5' end of the linker oligonucleotide is fused to the 3' end of the first gene, and the 3' end of the linker is fused to the 5' end of the second gene. Any number of genes can be connected in tandem array to encode multi-functional fusion proteins using the serine-rich polypeptide linker of the present invention. The entire fused gene can be transfected into a host cell by means of an appropriate expression vector.

In a preferred embodiment of the present invention, amino acid sequences mimicking the light (VL) and heavy ($V_H$) chain variable regions of an antibody are linked to form a single chain antibody binding site (sFv) which preferably is free of immunoglobulin constant region. Single chain antibody binding sites are described in detail, for example, in U.S. Pat. No. 5,019,513, the disclosure of which is incorporated herein by reference. A particularly effective serine-rich linker for an sFv protein is a linker having the following amino acid sequence:

(sequence ID No. 1)

—Ser—Gly—Ser—Ser—Ser—Ser—Gly—Ser—Ser—Ser—Ser—Gly—Ser—.

That is, in this embodiment y=2; Ser, Gly precedes the modular sequences, and Ser follows them. The serine-rich linker joins the $V_H$ with the $V_L$ (or vice versa) to produce a novel sFv fusion protein having substantially increased solubility, and resistance to lysis by endogenous proteases.

A preferred genus of linkers comprises a sequence having the formula:

(Sequence ID No.3 residues 3–7)

(X, X, X, X, Gly)$_y$

Where up to two Xs in each unit can be Thr, the remaining Xs are Ser, and y in between 1 and 5.

A method for producing a sFv is described in PCT Application No. US88/01737, the teachings of which are incorporated herein by reference. In general, the gene encoding the variable region from the heavy chain ($V_H$) of an antibody is connected at the DNA level to the variable region of the light chain ($V_L$) by an appropriate oligonucleotide. Upon translation, the resultant hybrid gene forms a single polypeptide chain comprising the two variable domains bridged by a linker peptide.

The sFv fusion protein comprises a single polypeptide chain with the sequence $V_H$-<linker>-$V_L$ or $V_L$-<linker>-$V_H$, as opposed to the classical Fv heterodimer of $V_H$ and $V_L$. About ¾ of each variable region polypeptide sequence is partitioned into four framework regions (FRs) that form a scaffold or support structure for the antigen binding site, which is constituted by the remaining residues defining three complementary determining regions (CDRs) which form loops connecting the FRs. The sFv is thus preferably composed of 8 FRs, 6 CDRs, and a linker segment, where the $V_H$ sequence can be abbreviated as:

FR1-H1-FR2-H2-FR3-H3-FR4;

and the $V_L$ sequence as

FR1-L1-FR2-L2-FR3-L3-FR4.

The predominant secondary structure in immunoglobulin V regions is the twisted β-sheet. A current interpretation of Fv architecture views the FRs as forming two concentric β-barrels, with the CDR loops connecting antiparallel β-strands of the inner barrel. The CDRs of a given murine monoclonal antibody may be grafted onto the FRs of human Fv regions in a process termed "humanization" or CDR replacement. Humanized antibodies promise minimal immunogenicity when sFv fusion proteins are administered to patients. Humanized single chain biosynthetic antibody binding sites, and how to make and use them, are described in detail in U.S. Pat. No. 5,019,513, as are methods of producing various other FR/CDR chimerics.

The general features of a viable peptide linker for an sFv fusion protein are governed by the architecture and chemistry of Fv regions. It is known that the sFv may be assembled in either domain order, $V_H$-linker-$V_L$ or $V_L$-linker-$V_H$, where the linker bridges the gap between the carboxyl (C) and amino (N) termini of the respective domains. For purposes of sFv design, the C-terminus of the amino-terminal $V_H$ or $V_L$ domain is considered to be the last residue of that sequence which is compactly folded, corresponding approximately to the end of the canonical V region sequence. The amino-terminal V domain is thus defined to be free of switch region residues that link the variable and constant domains of a given H or L chain, which makes the linker sequence an architectural element in sFv structure that corresponds to bridging residues, regardless of their origin. In several examples, fused sFv constructs have incorporated residues from the switch region, even extending into the first constant domain.

In principle, sFv proteins may be constructed to incorporate the Fv region of any monoclonal antibody regardless of its class or antigen specificity. Departures from parent V region sequences may involve changes in CDRs to modify antigen affinity or specificity, or to redefine complementarity, as well as wholesale alteration of framework regions to effect humanization of the sFv or for other purposes. In any event, an effective assay, e.g., a binding assay, must be available for the parent antibody and its sFv analogue. Design of such an assay is well within the skill of the art. Fusion proteins such as sFv immunotoxins intrinsically provide an assay by their toxicity to target cells in culture.

The construction of a single-chain Fv typically is accomplished in two or three phases: (1) isolation of cDNA for the variable regions; (2) modification of the isolated $V_H$ and $V_L$ domains to permit their joining to form a single chain via a linker; (3) expression of the single-chain Fv protein. The assembled sFv gene may then be progressively altered to modify sFv properties. *Escherichia coli* (*E. coli*) has generally been the source of most sFv proteins although other expression systems can be used to generate sFv proteins.

The $V_H$ and $V_L$ genes for a given monoclonal antibody are most conveniently derived from the cDNA of its parent hybridoma cell line. Cloning of $V_H$ and $V_L$ from hybridoma cDNA has been facilitated by library construction kits using lambda vectors such as Lambda ZAP$^R$ (Stratagene). If the nucleotide and/or amino acid sequences of the V domains are known, then the gene or the protein can be made synthetically. Alternatively, a semisynthetic approach can be taken by appropriately modifying other available cDNA clones or sFv genes by site-directed mutagenesis. Many alternative DNA probes have been used for V gene cloning from hybridoma cDNA libraries. Probes for constant regions have general utility provided that they match the class of the relevant heavy or light chain constant domain. Unrearranged genomic clones containing the J-segments have even broader utility, but the extent of sequence homology and hybridization stringency may be unknown. Mixed pools of synthetic oligonucleotides based on the J-regions of known amino acid sequence have been used. If the parental myeloma fusion partner was transcribing an endogenous immunoglobulin gene, the authentic clones for the V genes of interest should be distinguished from the genes of endogenous origin by examining their DNA sequences in a Genbank homology search.

The cloning steps described above may be simplified by the use of polymerase chain reaction (PCR) technology. For example, immunoglobulin cDNA can be transcribed from the monoclonal cell line by reverse transcriptase prior to amplification by Tag polymerase using specially designed primers. Primers used for isolation of V genes may also contain appropriate restriction sequences to speed sFv and fusion protein assembly. Extensions of the appropriate primers preferably also should encode parts of the desired linker sequence such that the PCR amplification products of $V_H$ and $V_L$ genes can be mixed to form the single-chain Fv gene directly. The application of PCR directly to human peripheral blood lymphocytes offers the opportunity to clone human V regions directly in bacteria. See., Davis et al. *Biotechnology*, 9, (2):165–169 (1991).

Refinement of antibody binding sites is possible by using filamentous bacteriophage that allow the expression of peptides or polypeptides on their surface. These methods have permitted the construction of phage antibodies that express functional sFv on their surface as well as epitope libraries that can be searched for peptides that bind to particular combining sites. With appropriate affinity isolation steps, this sFv-phage methodology offers the opportunity to generate mutants of a given sFv with desired changes in specificity and affinity as well as to provide for a refinement process in successive cycles of modification. See McCafferty et al., *Nature*, 348:552 (1990), Parmely et al. Gene, 38:305 (1988), Scott et al. *Science*, 249:386 (1990), Devlin et al. *Science*, 249:404 (1990)., and Cwirla et al., *Proc. Nat. Acad. Sci. U.S.A.*, 87:6378 (1990).

The placement of restriction sites in an sFv gene can be standardized to facilitate the exchange of individual $V_H$, $V_L$ linker elements, or leaders (See U.S. Pat. No. 5,019,513, supra). The selection of particular restriction sites can be governed by the choice of stereotypical sequences that may be fused to different sFv genes. In mammalian and bacterial secretion, secretion signal peptides are cleaved from the N-termini of secreted proteins by signal peptidases. The production of sFv proteins by intracellular accumulation in inclusion bodies also may be exploited. In such cases a restriction site for gene fusion and corresponding peptide cleavage site are placed at the N-terminus of either $V_H$ or $V_L$. Frequently a cleavage site susceptible to mild acid for release of the fusion leader is chosen.

In a general scheme, a SacI site serves as an adapter at the C-Terminal end of $V_H$. A large number of $V_H$ regions end in the sequence -Val-Ser-Ser-, which is compatible with the codons for a SacI site (G AGC TCT), to which the linker may be attached. The linker of the present invention can be arranged such that a -Gly-Ser- is positioned at the C-terminal end of the linker encoded by GGA-TCC to generate a BamHI site, which is useful provided that the same site is not chosen for the beginning of $V_H$.

Alternatively, an XhoI site (CTCGAG) can be placed at the C-terminal end of the linker by including another serine to make a -Gly-Ser-Ser- sequence that can be encoded by GGC-TCG-AGN-, which contains the XhoI site. For sFv genes encoding $V_H$-Linker-$V_L$, typically a PstI site is positioned at the 3' end of the $V_L$ following the new stop condon, which forms a standard site for ligation to expression vectors. If any of these restriction sites occur elsewhere in the cDNA, they can be removed by silent base changes using site directed mutagenesis. Similar designs can be used to develop a standard architecture for $V_L$-$V_H$ constructions.

Expression of fusion proteins in *E. coli* as insoluble inclusion bodies provides a reliable method for producing sFv proteins. This method allows for rapid evaluation of the level of expression and activity of the sFv fusion protein while eliminating variables associated with direct expression or secretion. Some fusion partners tend not to interfere with antigen binding which may simplify screening for sFv fusion protein during purification. Fusion protein derived from inclusion bodies must be purified and refolded in vitro to recover antigen binding activity. Mild acid hydrolysis can be used to cleave a labile Asp-Pro peptide bond between the leader and sFv yielding proline at the sFv amino terminus. In other situations, leader cleavage can rely on chemical or enzymatic hydrolysis at specifically engineered sites, such as CNBr cleavage of a unique methionine, hydroxylamine cleavage of the peptide bond between Asn-Gly, and enzymatic digestion at specific cleavage sites such as those recognized by factor Xa, enterokinase or V8 protease.

Direct expression of intracellular sFv proteins which yields the desired sFv without a leader attached is possible for single-chain Fv analogues and sFv fusion proteins. Again, the isolation of inclusion bodies must be followed by refolding and purification. This approach avoids the steps needed for leader removal but direct expression can be complicated by intracellular proteolysis of the cloned protein.

The denaturation transitions of Fab fragments from polyclonal antibodies are known to cover a broad range of denaturant. The denaturation of monoclonal antibody Fab fragments or component domains exhibit relatively sharp denaturation transitions over a limited range of denaturant. Thus, sFv proteins can be expected to differ similarly covering a broad range of stabilities and denaturation properties which appear to be paralleled by their preferences for distinct refolding procedures. Useful refolding protocols include dilution refolding, redox refolding and disulfide restricted refolding. In general, all these procedures benefit from the enhanced solubility conferred by the serine-rich linker of the present invention.

Dilution refolding relies on the observation that fully reduced and denatured antibody fragments can refold upon removal of denaturant and reducing agent with recovery of specific binding activity. Redox refolding utilizes a glutathione redox couple to catalyze disulfide interchange as the protein refolds into its native state. For an sFv protein having a prior art linker such as (GlyGlyGLyGlySer)$_3$, the protein is diluted from a fully reduced state in 6M urea into 3M urea+25 mM Tris-HCL+10 mM EDTA, pH 8, to yield a final concentration of approximately 0.1 mg/ml. In a representative protein, the sFv unfolding transition begins around 3M urea and consequently the refolding buffer represents near-native solvent conditions. Under these conditions, the protein can presumably reform approximations to the V domain structures wherein rapid disulfide interchange can occur until a stable equilibrium is attained. After incubation at room temperature for 16 hours, the material is dialyzed first against urea buffer lacking glutathione and then against 0.01M sodium acetate+0.25M urea, pH 5.5.

In contrast to the sFv protein having the prior art linker described above, with the same sFv protein, but having a serine-rich linker of the present invention, the 3M urea-glutathione refolding solution can be dialyzed directly into 0.05M potassium phosphate, pH 7, 0.15 NaCl (PBS).

Disulfide restricted refolding offers still another route to obtaining active sFv which involves initial formation of intrachain disulfides in the fully denatured sFv. This capitalizes on the favored reversibility of antibody refolding when disulfides are kept intact. Disulfide crosslinks should restrict the initial refolding pathways available to the molecule as well as other residues adjacent to cysteinyl residues that are close in the native state. For chains with the correct disulfide paring the recovery of a native structure should be favored while those chains with incorrect disulfide pairs must necessarily produce non-native species upon removal of denaturant. Although this refolding method may give a lower yield than other procedures, it may be able to tolerate higher protein concentrations during refolding.

Proteins secreted into the periplasmic space or into the culture medium appear to refold properly with formation of the correct disulfide bonds. In the majority of cases the signal peptide sequence is removed by a bacterial signal peptidase to generate a product with its natural amino terminus. Even though most secretion systems currently give considerably lower yields than intracellular expression, the rapidity of obtaining correctly folded and active sFv proteins can be of decisive value for protein engineering. The ompA or pelB signal sequence can be used to direct secretion of the sFv.

If some sFv analogues or fusion proteins exhibit lower binding affinities than the parent antibody, further purification of the sFv protein or additional refinement of antigen binding assays may be needed. On the other hand, such sFv behavior may require modification of protein design. Changes at the amino-termini of V domains may on occasion perturb a particular combining site. Thus, if an sFv were to exhibit a lower affinity for antigen than the parent Fab fragment, one could test for a possible N-terminal perturbation effect. For instance, given a $V_L$-$V_H$ that was suspect, the $V_H$-$V_L$ construction could be made and tested. If the initially observed perturbation were changed or eliminated in the alternate sFv species, then the effect could be traced to the initial sFv design.

The invention will be understood further from the following nonlimiting examples.

EXAMPLES

Example 1

Preparation and Evaluation of an Anti-digoxin 26-10 sFv Having a Serine-rich Linker An anti-digoxin 26-10 sFv containing a serine-rich peptide linker (Sequence No. 1, identified below) of the present invention was prepared as follows:

(Sequence ID No.1)

—Ser—Gly—Ser—Ser—Ser—Ser—Gly—Ser—Ser—Ser—Ser—Gly—Ser—
  1    2    3    4    5    6    7    8    9   10   11   12   13

A set of synthetic oligonucleotides was prepared using phosphoramidite chemistry on a Cruachem DNA synthesizer, model PS250. The nucleotide sequence in the appropriate reading frame encodes the polypeptide from 1–12 while residue 13 is incorporated as part of the Bam Hl site that forms upon fusion to the downstream Ban Hl fragment that encodes $V_L$; and the first serine residue in the linker was attached to a serine at the end of the 26-10 $V_H$ region of the antibody. This is shown more clearly in Sequence ID Nos. 4 and 5.

The synthetic oligonucleotide sequence which was used in the cassette mutagenesis was as follows:

Sequence ID No.2

```
    CC TCC GGA TCT TCA TCT AGC GGT TCC AGC AGT G
TCG AGG AGG CCT AGA AGT AGA TCG CCA AGG RCG TCA CCT AG
SacI                                              BamHI
```

The complementary oligomers, when annealed to each other, present a cohesive end of a SacI site upstream and a BamHI site downstream.

The nucleotide sequence was designed to contain useful 6-base restriction sites which will allow combination with other single chain molecules and additional modifications of the leader. The above-described synthetic oligonucleotides were assembled with the $V_H$ and $V_L$ regions of the anti-digoxin 26-10 gene as follows:

A pUC plasmid containing the 26-10 sFv gene (disclosed in PCT International Publication No. WO 88/09344) containing a (Gly-Gly-Gly-Gly-Ser)$_n$ linker between a SacI site at the end of the $V_H$ region and a unique BamHI site which had been inserted at the beginning of $V_L$ region was opened at SacI and BamHI to release the sequence encoding for the prior art linker and to accept the oligonucleotides defined by Sequence No. 2. The resulting plasmid was called pH899.

The new 26-10 sFv gene of pH899 was inserted into an expression vector, pH895, for fusion with a modified fragment B (MFB) of staphlococcal protein A. (See Sequence ID No. 4.) The modified FB leader has glutamyl resides at positions FB-36 and FB-37 instead of 2 aspartyl residues, which reduces unwanted ancillary cleavage during acid treatment. The modified pH895 is essentially equivalent to pC105 (except for the slightly modified leader) as previously described in Biochemistry, 29(35):8024–8030 (1990). The assembly was done by replacing the old sFv fragment with the new sFv between XbaI (in $V_H$) and PstI (at the end of sFv) in the expression plasmid pH895, opened at unique XbaI and PstI sites. The resulting new expression vector was named pH908. An expression vector utilizing an MLE-MFB leader was constructed as follows.

The mFB-sFv gene was retrieved by treating pH908 with EcoRI and PstI and inserted into a trp expression vector containing the modified trp LE leader peptide (MLE) producing plasmid pH912. This vector resembled essentially the pD312 plasmid as described in PNAS, 85: 5879–5883 (1988) but having removed from it the EcoRI site situated between the Tet-R gene and the SspI site. Plasmid pH912 contained the MLE-mFB-sFv gene shown in sequence 4. The MLE starts at the N-terminus of the protein and ends at the glutamic acid residue, amino acid residue 59. The mFB leader sequence starts at the methionine residue, amino acid residue 61, and ends at the aspartic acid residue, amino acid residue 121. Phenylanine residue 60 is technically part of the Eco RI restriction site sequence at the junction of the MLE and mFB.

Expression of sFv transfected into E. coli (strain JM101) by the plasmid pH912 was under control of the trp promoter. E. coli was transformed by pH912 under selection by tetracycline. Expression was induced in M9 minimal medium by addition,of indole acrylic acid (10 µg/ml) at a cell density with $A_{600}$=1 resulting in high level expression and formation of inclusion bodies which were harvested from cell paste.

After expression in E. coli of the sFv protein containing the novel linker of the present invention, the resultant cells were suspended in 25 mM Tris-HCl, pH 8, and 10mmM EDTA treated with 0.1% lysozyme overnight, sonicated at a high setting for three 5 minute periods in the cold, and spun in a preparative centrifuge at 11,200×g for 30 minutes. For large scale preparation of inclusion bodies, the cells are concentrated by ultrafiltration and then lysed with a laboratory homogenizer such as with model 15MR, APV homogenizer manufactured by Gaulin, Inc. The inclusion bodies are then collected by centrifugation. The resultant pellet was then washed with a buffer containing 3M urea, 25 mM Tris-HCl, pH8, and 10 mEDTA.

The purification of the 26-10 sFv containing the linker of the present invention from the MLE-mFB-sFv fusion protein was then accomplished according to the following procedure:

1) Solubilization of Fusion Protein in Guanidine Hydrochloride

The MLE-mFB-sFv inclusion bodies were weighed and were then dissolved in a 6.7M GuHCl (guanidine hydrochloride) which had been dissolved in 10% acetic acid. An amount of GuHCl equal to the weight of the recovered inclusion bodies was then added to the solution and dissolved to compensate for the water present in the inclusion body pellet.

2) Acid Cleavage of the Unique Asp-PrO Bond at the Junction of the Leader and 26-10 sFv The Asp-Pro bond (amino acid residues 121 and 122 of Sequence Nos. 4 and 5) was cleaved in the following manner. Glacial acetic acid was added to the solution of step 1 to 10% of the total volume of the solution. The pH of the solution was then adjusted to 2.5 with concentrated HCl. This solution was then incubated at 37° C. for 96 hours. The reaction was stopped by adding 9 volumes of cold ethanol, stored at −20° C. for several hours, followed by centrifugation to yield a pellet of precipitated 26-10 sFv and uncleaved fusion protein. The heavy chain variable region of the sFv molecule extended from amino acid residue 123 to 241; the linker included amino acid residues 242 to 254; and the variable light region extended from amino acid residue 255 to 367 of Sequence Nos. 4 and 5. Note also that Sequence No. 6 and 7 shows a similar sFv starting with methionine at residues 1 followed by $V_H$ (residues 2–120), linker (121–133), and $V_L$ (134–246). This gene product was expressed directly by the T7 expression system with formation of inclusion bodies.

3) Re-dissolution of Cleavage Products

The precipitated sFv cleavage mixture from step 2 was weighed and dissolved in a solution of 6M GuHl+25 mM Tris HCl+10 mM EDTA having a pH of 8.6. Solid GuHCl in an amount equal to the weight of the sFv cleavage mixture from step two was then added and dissolved in the solution. The pH of the solution was then adjusted to 8.6 and dithiothreitol was added to the solution such that the resultant solution contained 10 mM dithiothreitol. The solution was then incubated at room temperature for 5 hours.

4) Renaturation of 26-10 sFv

The solution obtained from step 3 was then diluted 70-fold to a concentration of about 0.2mg of protein/ml with a buffer solution containing 3M urea, 25 mM Tris-HCl, pH 8, 10 mM EDTA 1 mM oxidized gluthathione, 0.1 mM reduced gluthathione, and incubated at room temperature for 16 hours. The resultant protein solution was then dialyzed in the cold against PBSA to complete the refolding of the sFv protein.

(5) Affinity Purification of the Active Anti-digoxin 26-10 sFv

The refolded protein from step 4 was loaded onto a column containing ouabain-amine-Sepharose 4B, and the column was washed successively with PBSA, followed by two column volumes of 1M NaCl in PBSA and then again with PBSA to remove salt. Finally, the active protein was displaced from the resin by 20 mM ouabain in PBSA. Absorbance measurements at 280 nm indicated which fractions contained active protein. However, the spectra of the protein and ouabain overlap. Consequently, ouabain was removed by exhaustive dialysis against PBSA in order to accurately quantitate the protein yield.

6) Removal of Uncleaved Fusion Protein and the MLE-mFB Leader

Finally, the solution from step 5 containing the active refolded protein (sFv and MLE-mFB-sFv) was chromatographed on an IgG-Sepharose column in PBSA buffer. The uncleaved MLE-mFB-sFv protein bound to the immobilized immunoglobulin and the column effluent contained essentially pure sFv.

In conclusion, the incorporation of a serine-rich peptide linker of 13 residues [Ser-Gly-(Ser-Ser-Ser-Ser-Gly) $_2$-Ser-] in the 26-10 sFv yielded significant improvements over the 26-10 sFv with a glycine-rich linker of 15 residues, [-(Gly-Gly-Gly-Gly-Ser)$_3$].

The serine-rich peptide linker of the present invention results in a number of improvements over the previous peptide linkers including:

1. Refolding and storage conditions are consistent with normal serum conditions, thereby making applications to pharmacology and toxicology accessible. The 26-10 sFv can be renatured in PBS (0.05M potassium phosphate, 0.15M NaCl, pH 7.0); 0.03% azide is added as a bacteriostatic agent for laboratory purposes but would be excluded in any animal or clinical applications. The old linker, 26-10 sFv had to be renatured into 0.01M sodium acetate, pH 5.5, with 0.25M urea added to enhance the level of active protein.

2. Solubility was vastly improved from a limit of about 5OD$_{280}$ units per ml (about 3 mg/ml) to 52 OD$_{280}$ units per ml (about 33 mg/ml), and possibly greater in buffers other than PBSA. The highly concentrated protein solution was measured directly with a 0.2 mm path length cell. The protein concentration was estimated by multiplying by 50 the absorptions at 280 nm, subtracting twice the scattering absorbance at 333 nm, which yields a corrected A280 of about 52 units per ml.

3. Fidelity of the antigen binding site was retained by the new serine-rich linker 26-10 sFv, which is consistent with an uncharged linker peptide that has minimal interactions with the V domains.

4. Enhanced stability at normal serum pH and ionic strength. In PSBSA, 26-10 sFv with the (GGGGS)$_3$ linker loses binding activity irreversibly whereas the 26-10 sFv containing the new serine-rich linker is completely stable in PBSA.

5. Enhanced resistance to proteolysis. The presence of the serine-rich linker improves resistance to endogenous proteases in vivo, which results in a longer plasma/half-life of the fusion protein.

Example 2

Preparation of a Fusion Protein Having a Serine Rich Linker

A fusion protein was prepared containing a serine rich linker linking two unrelated proteins. A fusion gene was constructed as described in Example 1 above, except that in lieu of the $V_L$ and $V_H$ genes described in Example 1, genes encoding the following proteins were fused: the dominant dhfr gene (Sequence No. 8, residues 1–576) and the neogene (Sequence No. 8, residues 621–1416) were fused with a linker having the sequence:

(Sequence No.8, nucleotide 577–620, amino acid residues 193–207)

—Ser—Ser—Ser—Gly—Ser—Ser—Ser—Ser—Gly—Ser—Ser—Ser—Ser—

Gly—Ser—

The four residues SVTV (numbers 189–192 of Seq. ID No. 8) can be regarded as part of the linker. These were left over from the sFv from which the linker sequences used in this example was derived. The resulting protein was a functional fusion protein encoding domains from two unrelated proteins which retained the activity of both. Thus, this DNA included on a plasmid inparts to successfully transfected cells resistance to both methotrexate, due to the action of the DHFR enzyme, and to neomycin, due to the action of the neo expression product.

Equivalents

One skilled in the art will recognize many equivalents to the specific embodiments described herein. Such equivalents are intended to be encompassed by the following claims.

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 1..13
        ( D ) OTHER INFORMATION: /note="(SER)4-GLY LINKER. THE
            REPEATING SEQUENCE "(SER)4-GLY"(E.G., RES. 3-7)
            MAY BE REPEATED MULTIPLE TIMES (SEE SPECIFICATION.)

( x i ) SEQUENCE DESCRIPTION: SEQ ID NO:1:

```
Ser  Gly  Ser  Ser  Ser  Ser  Gly  Ser  Ser  Ser  Ser  Gly  Ser
 1             5                        10
```

( 2 ) INFORMATION FOR SEQ ID NO:2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: syn DNA ( i x ) FEATURE:
        ( A ) NAME/KEY: misc_feature
        ( B ) LOCATION: 1..36
        ( D ) OTHER INFORMATION: /note="LINKER SEQUENCE (TOP
            STRAND)"

( x i ) SEQUENCE DESCRIPTION: SEQ ID NO:2:

CCTCCGGATC TTCATCTAGC GGTTCCAGCT CGAGTG                      36

( 2 ) INFORMATION FOR SEQ ID NO:3:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
    ( A ) NAME/KEY: Peptide
    ( B ) LOCATION: 1..13
    ( D ) OTHER INFORMATION: /note="(XAA)4-GLY LINKER, WHERE
    RES.3-7 ARE THE REPEATING UNIT AND UP TO 2 OF THE XAA'S
    IN REPEAT UNIT CAN BE THR, THE REMAINDER SER.

( x i ) SEQUENCE DESCRIPTION: SEQ ID NO:3:

```
Xaa Gly Xaa Xaa Xaa Xaa Gly Xaa Xaa Xaa Xaa Gly Xaa
 1               5                      10
```

( 2 ) INFORMATION FOR SEQ ID NO:4:

( i ) SEQUENCE CHARACTERISTICS:
        ( A ) LENGTH: 1110 base pairs
        ( B ) TYPE: nucleic acid
        ( C ) STRANDEDNESS: single
        ( D ) TOPOLOGY: linear ( i i ) MOLECULE TYPE: syn DNA ( i x ) FEATURE:
        ( A ) NAME/KEY: CDS
        ( B ) LOCATION: 1..1101

( x i ) SEQUENCE DESCRIPTION: SEQ ID NO:4:

```
ATG AAA GCA ATT TTC GTA CTG AAA GGT TCA CTG GAC AGA GAT CTG GAC      48
Met Lys Ala Ile Phe Val Leu Lys Gly Ser Leu Asp Arg Asp Leu Asp
 1               5                  10                  15

TCT CGT CTG GAT CTG GAC GTT CGT ACC GAC CAC AAA GAC CTG TCT GAT      96
Ser Arg Leu Asp Leu Asp Val Arg Thr Asp His Lys Asp Leu Ser Asp
                20                  25                  30

CAC CTG GTT CTG GTC GAC CTG GCT CGT AAC GAC CTG GCT CGT ATC GTT     144
His Leu Val Leu Val Asp Leu Ala Arg Asn Asp Leu Ala Arg Ile Val
             35                  40                  45

ACT CCC GGG TCT CGT TAC GTT GCG GAT CTG GAA TTC ATG GCT GAC AAC     192
Thr Pro Gly Ser Arg Tyr Val Ala Asp Leu Glu Phe Met Ala Asp Asn
         50                  55                  60

AAA TTC AAC AAG GAA CAG CAG AAC GCG TTC TAC GAG ATC TTG CAC CTG     240
Lys Phe Asn Lys Glu Gln Gln Asn Ala Phe Tyr Glu Ile Leu His Leu
 65                  70                  75                  80

CCG AAC CTG AAC GAA GAG CAG CGT AAC GGC TTC ATC CAA AGC CTG AAA     288
Pro Asn Leu Asn Glu Glu Gln Arg Asn Gly Phe Ile Gln Ser Leu Lys
                 85                  90                  95

GAA GAG CCG TCT CAG TCT GCG AAT CTG CTA GCG GAT GCC AAG AAA CTG     336
Glu Glu Pro Ser Gln Ser Ala Asn Leu Leu Ala Asp Ala Lys Lys Leu
             100                 105                 110

AAC GAT GCG CAG GCA CCG AAA TCG GAT CCC GAA GTT CAA CTG CAA CAG     384
Asn Asp Ala Gln Ala Pro Lys Ser Asp Pro Glu Val Gln Leu Gln Gln
         115                 120                 125

TCT GGT CCT GAA TTG GTT AAA CCT GGC GCC TCT GTG CGC ATG TCC TGC     432
Ser Gly Pro Glu Leu Val Lys Pro Gly Ala Ser Val Arg Met Ser Cys
    130                 135                 140

AAA TCC TCT GGG TAC ATT TTC ACC GAC TTC TAC ATG AAT TGG GTT CGC     480
Lys Ser Ser Gly Tyr Ile Phe Thr Asp Phe Tyr Met Asn Trp Val Arg
145                 150                 155                 160

CAG TCT CAT GGT AAG TCT CTA GAC TAC ATC GGG TAC ATT TCC CCA TAC     528
Gln Ser His Gly Lys Ser Leu Asp Tyr Ile Gly Tyr Ile Ser Pro Tyr
                165                 170                 175

TCT GGG GTT ACC GGC TAC AAC CAG AAG TTT AAA GGT AAG GCG ACC CTT     576
Ser Gly Val Thr Gly Tyr Asn Gln Lys Phe Lys Gly Lys Ala Thr Leu
            180                 185                 190

ACT GTC GAC AAA TCT TCC TCA ACT GCT TAC ATG GAG CTG CGT TCT TTG     624
Thr Val Asp Lys Ser Ser Ser Thr Ala Tyr Met Glu Leu Arg Ser Leu
        195                 200                 205
```

| | | | | | | | | | | | | | | | | |
|---|---|---|---|---|---|---|---|---|---|---|---|---|---|---|---|---|
| ACC | TCT | GAG | GAC | TCC | GCG | GTA | TAC | TAT | TGC | GCG | GGC | TCC | TCT | GGT | AAC | 672 |
| Thr | Ser | Glu | Asp | Ser | Ala | Val | Tyr | Tyr | Cys | Ala | Gly | Ser | Ser | Gly | Asn | |
| | 210 | | | | 215 | | | | | 220 | | | | | | |
| AAA | TGG | GCC | ATG | GAT | TAT | TGG | GGT | CAT | GGT | GCT | AGC | GTT | ACT | GTG | AGC | 720 |
| Lys | Trp | Ala | Met | Asp | Tyr | Trp | Gly | His | Gly | Ala | Ser | Val | Thr | Val | Ser | |
| 225 | | | | | 230 | | | | | 235 | | | | | 240 | |
| TCC | TCC | GGA | TCT | TCA | TCT | AGC | GGT | TCC | AGC | TCG | AGT | GGA | TCC | GAC | GTC | 768 |
| Ser | Ser | Gly | Ser | Ser | Ser | Ser | Gly | Ser | Ser | Ser | Ser | Gly | Ser | Asp | Val | |
| | | | | 245 | | | | | 250 | | | | | 255 | | |
| GTA | ATG | ACC | CAG | ACT | CCG | CTG | TCT | CTG | CCG | GTT | TCT | CTG | GGT | GAC | CAG | 816 |
| Val | Met | Thr | Gln | Thr | Pro | Leu | Ser | Leu | Pro | Val | Ser | Leu | Gly | Asp | Gln | |
| | | | 260 | | | | | 265 | | | | | 270 | | | |
| GCT | TCT | ATT | TCT | TGC | CGC | TCT | TCC | CAG | TCT | CTG | GTC | CAT | TCT | AAT | GGT | 864 |
| Ala | Ser | Ile | Ser | Cys | Arg | Ser | Ser | Gln | Ser | Leu | Val | His | Ser | Asn | Gly | |
| | | 275 | | | | | 280 | | | | | 285 | | | | |
| AAC | ACT | TAC | CTG | AAC | TGG | TAC | CTG | CAA | AAG | GCT | GGT | CAG | TCT | CCG | AAG | 912 |
| Asn | Thr | Tyr | Leu | Asn | Trp | Tyr | Leu | Gln | Lys | Ala | Gly | Gln | Ser | Pro | Lys | |
| | 290 | | | | | 295 | | | | | 300 | | | | | |
| CTT | CTG | ATC | TAC | AAA | GTC | TCT | AAC | CGC | TTC | TCT | GGT | GTC | CCG | GAT | CGT | 960 |
| Leu | Leu | Ile | Tyr | Lys | Val | Ser | Asn | Arg | Phe | Ser | Gly | Val | Pro | Asp | Arg | |
| 305 | | | | | 310 | | | | | 315 | | | | | 320 | |
| TTC | TCT | GGT | TCT | GGT | TCT | GGT | ACT | GAC | TTC | ACC | CTG | AAG | ATC | TCT | CGT | 1008 |
| Phe | Ser | Gly | Ser | Gly | Ser | Gly | Thr | Asp | Phe | Thr | Leu | Lys | Ile | Ser | Arg | |
| | | | | 325 | | | | | 330 | | | | | 335 | | |
| GTC | GAG | GCC | GAA | GAC | CTG | GGT | ATC | TAC | TTC | TGC | TCT | CAG | ACT | ACT | CAT | 1056 |
| Val | Glu | Ala | Glu | Asp | Leu | Gly | Ile | Tyr | Phe | Cys | Ser | Gln | Thr | Thr | His | |
| | | | 340 | | | | | 345 | | | | | 350 | | | |
| GTA | CCG | CCG | ACT | TTT | GGT | GGT | GGC | ACC | AAG | CTC | GAG | ATT | AAA | CGT | | 1101 |
| Val | Pro | Pro | Thr | Phe | Gly | Gly | Gly | Thr | Lys | Leu | Glu | Ile | Lys | Arg | | |
| | | 355 | | | | | 360 | | | | | 365 | | | | |
| TAACTGCAG | | | | | | | | | | | | | | | | 1110 |

( 2 ) INFORMATION FOR SEQ ID NO:5:

( i ) SEQUENCE CHARACTERISTICS:
        ( A ) LENGTH: 367 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

| | | | | | | | | | | | | | | |
|---|---|---|---|---|---|---|---|---|---|---|---|---|---|---|
| Met | Lys | Ala | Ile | Phe | Val | Leu | Lys | Gly | Ser | Leu | Asp | Arg | Asp | Leu | Asp |
| 1 | | | | 5 | | | | | 10 | | | | | 15 | |
| Ser | Arg | Leu | Asp | Leu | Asp | Val | Arg | Thr | Asp | His | Lys | Asp | Leu | Ser | Asp |
| | | | 20 | | | | | 25 | | | | | 30 | | |
| His | Leu | Val | Leu | Val | Asp | Leu | Ala | Arg | Asn | Asp | Leu | Ala | Arg | Ile | Val |
| | | | 35 | | | | 40 | | | | | 45 | | | |
| Thr | Pro | Gly | Ser | Arg | Tyr | Val | Ala | Asp | Leu | Glu | Phe | Met | Ala | Asp | Asn |
| | | 50 | | | | | 55 | | | | | 60 | | | |
| Lys | Phe | Asn | Lys | Glu | Gln | Gln | Asn | Ala | Phe | Tyr | Glu | Ile | Leu | His | Leu |
| 65 | | | | | 70 | | | | | 75 | | | | | 80 |
| Pro | Asn | Leu | Asn | Glu | Glu | Gln | Arg | Asn | Gly | Phe | Ile | Gln | Ser | Leu | Lys |
| | | | | 85 | | | | | 90 | | | | | 95 | |
| Glu | Glu | Pro | Ser | Gln | Ser | Ala | Asn | Leu | Leu | Ala | Asp | Ala | Lys | Lys | Leu |
| | | | 100 | | | | | 105 | | | | | 110 | | |
| Asn | Asp | Ala | Gln | Ala | Pro | Lys | Ser | Asp | Pro | Glu | Val | Gln | Leu | Gln | Gln |
| | | | 115 | | | | 120 | | | | | 125 | | | |
| Ser | Gly | Pro | Glu | Leu | Val | Lys | Pro | Gly | Ala | Ser | Val | Arg | Met | Ser | Cys |

|     |     |     |     |     | 130 |     |     |     |     | 135 |     |     |     |     | 140 |     |
|-----|-----|-----|-----|-----|-----|-----|-----|-----|-----|-----|-----|-----|-----|-----|-----|-----|

Lys Ser Ser Gly Tyr Ile Phe Thr Asp Phe Tyr Met Asn Trp Val Arg
145                     150                     155                     160

Gln Ser His Gly Lys Ser Leu Asp Tyr Ile Gly Tyr Ile Ser Pro Tyr
                165                     170                     175

Ser Gly Val Thr Gly Tyr Asn Gln Lys Phe Lys Gly Lys Ala Thr Leu
            180                     185                     190

Thr Val Asp Lys Ser Ser Thr Ala Tyr Met Glu Leu Arg Ser Leu
        195                     200                     205

Thr Ser Glu Asp Ser Ala Val Tyr Tyr Cys Ala Gly Ser Ser Gly Asn
    210                     215                     220

Lys Trp Ala Met Asp Tyr Trp Gly His Gly Ala Ser Val Thr Val Ser
225                     230                     235                     240

Ser Ser Gly Ser Ser Ser Ser Gly Ser Ser Ser Ser Gly Ser Asp Val
                245                     250                     255

Val Met Thr Gln Thr Pro Leu Ser Leu Pro Val Ser Leu Gly Asp Gln
            260                     265                     270

Ala Ser Ile Ser Cys Arg Ser Ser Gln Ser Leu Val His Ser Asn Gly
        275                     280                     285

Asn Thr Tyr Leu Asn Trp Tyr Leu Gln Lys Ala Gly Gln Ser Pro Lys
    290                     295                     300

Leu Leu Ile Tyr Lys Val Ser Asn Arg Phe Ser Gly Val Pro Asp Arg
305                     310                     315                     320

Phe Ser Gly Ser Gly Ser Gly Thr Asp Phe Thr Leu Lys Ile Ser Arg
                325                     330                     335

Val Glu Ala Glu Asp Leu Gly Ile Tyr Phe Cys Ser Gln Thr Thr His
            340                     345                     350

Val Pro Pro Thr Phe Gly Gly Gly Thr Lys Leu Glu Ile Lys Arg
        355                     360                     365

(2) INFORMATION FOR SEQ ID NO:6:

(i) SEQUENCE CHARACTERISTICS:
        (A) LENGTH: 747 base pairs
        (B) TYPE: nucleic acid
        (C) STRANDEDNESS: single
        (D) TOPOLOGY: linear (ii) MOLECULE TYPE: syn DNA (ix) FEATURE:
        (A) NAME/KEY: CDS
        (B) LOCATION: 1..747

(xi) SEQUENCE DESCRIPTION: SEQ ID NO:6:

```
ATG GAA GTT CAA CTG CAA CAG TCT GGT CCT GAA TTG GTT AAA CCT GGC       48
Met Glu Val Gln Leu Gln Gln Ser Gly Pro Glu Leu Val Lys Pro Gly
 1               5                  10                  15

GCC TCT GTG CGC ATG TCC TGC AAA TCC TCT GGG TAC ATT TTC ACC GAC       96
Ala Ser Val Arg Met Ser Cys Lys Ser Ser Gly Tyr Ile Phe Thr Asp
                20                  25                  30

TTC TAC ATG AAT TGG GTT CGC CAG TCT CAT GGT AAG TCT CTA GAC TAC      144
Phe Tyr Met Asn Trp Val Arg Gln Ser His Gly Lys Ser Leu Asp Tyr
             35                  40                  45

ATC GGG TAC ATT TCC CCA TAC TCT GGG GTT ACC GGC TAC AAC CAG AAG      192
Ile Gly Tyr Ile Ser Pro Tyr Ser Gly Val Thr Gly Tyr Asn Gln Lys
         50                  55                  60

TTT AAA GGT AAG GCG ACC CTT ACT GTC GAC AAA TCT TCC TCA ACT GCT      240
Phe Lys Gly Lys Ala Thr Leu Thr Val Asp Lys Ser Ser Ser Thr Ala
 65                  70                  75                  80
```

```
TAC ATG GAG CTG CGT TCT TTG ACC TCT GAG GAC TCC GCG GTA TAC TAT      288
Tyr Met Glu Leu Arg Ser Leu Thr Ser Glu Asp Ser Ala Val Tyr Tyr
             85                  90                  95

TGC GCG GGC TCC TCT GGT AAC AAA TGG GCG ATG GAT TAT TGG GGT CAT      336
Cys Ala Gly Ser Ser Gly Asn Lys Trp Ala Met Asp Tyr Trp Gly His
            100                 105                 110

GGT GCT AGC GTT ACT GTG AGC TCC TCC GGA TCT TCA TCT AGC GGT TCC      384
Gly Ala Ser Val Thr Val Ser Ser Ser Gly Ser Ser Ser Ser Gly Ser
            115                 120                 125

AGC TCG AGT GGA TCC GAC GTC GTA ATG ACC CAG ACT CCG CTG TCT CTG      432
Ser Ser Ser Gly Ser Asp Val Val Met Thr Gln Thr Pro Leu Ser Leu
        130                 135                 140

CCG GTT TCT CTG GGT GAC CAG GCT TCT ATT TCT TGC CGC TCT TCC CAG      480
Pro Val Ser Leu Gly Asp Gln Ala Ser Ile Ser Cys Arg Ser Ser Gln
145                 150                 155                 160

TCT CTG GTC CAT TCT AAT GGT AAC ACT TAC CTG AAC TGG TAC CTG CAA      528
Ser Leu Val His Ser Asn Gly Asn Thr Tyr Leu Asn Trp Tyr Leu Gln
                165                 170                 175

AAG GCT GGT CAG TCT CCG AAG CTT CTG ATC TAC AAA GTC TCT AAC CGC      576
Lys Ala Gly Gln Ser Pro Lys Leu Leu Ile Tyr Lys Val Ser Asn Arg
            180                 185                 190

TTC TCT GGT GTC CCG GAT CGT TTC TCT GGT TCT GGT TCT GGT ACT GAC      624
Phe Ser Gly Val Pro Asp Arg Phe Ser Gly Ser Gly Ser Gly Thr Asp
            195                 200                 205

TTC ACC CTG AAG ATC TCT CGT GTC GAG GCC GAA GAC CTG GGT ATC TAC      672
Phe Thr Leu Lys Ile Ser Arg Val Glu Ala Glu Asp Leu Gly Ile Tyr
        210                 215                 220

TTC TGC TCT CAG ACT ACT CAT GTA CCG CCG ACT TTT GGT GGT GGC ACC      720
Phe Cys Ser Gln Thr Thr His Val Pro Pro Thr Phe Gly Gly Gly Thr
225                 230                 235                 240

AAG CTC GAG ATT AAA CGT TAA CTG CAG                                   747
Lys Leu Glu Ile Lys Arg
            245
```

( 2 ) INFORMATION FOR SEQ ID NO:7:

( i ) SEQUENCE CHARACTERISTICS:
        ( A ) LENGTH: 246 amino acids
        ( B ) TYPE: amino acid
        ( D ) TOPOLOGY: linear ( i i ) MOLECULE TYPE: protein ( x i ) SEQUENCE DESCRIPTION: SEQ ID NO:7:

```
Met Glu Val Gln Leu Gln Gln Ser Gly Glu Leu Val Lys Pro Gly
 1               5                  10                  15

Ala Ser Val Arg Met Ser Cys Lys Ser Ser Gly Tyr Ile Phe Thr Asp
             20                  25                  30

Phe Tyr Met Asn Trp Val Arg Gln Ser His Gly Lys Ser Leu Asp Tyr
            35                  40                  45

Ile Gly Tyr Ile Ser Pro Tyr Ser Gly Val Thr Gly Tyr Asn Gln Lys
        50                  55                  60

Phe Lys Gly Lys Ala Thr Leu Thr Val Asp Lys Ser Ser Ser Thr Ala
65                  70                  75                  80

Tyr Met Glu Leu Arg Ser Leu Thr Ser Glu Asp Ser Ala Val Tyr Tyr
             85                  90                  95

Cys Ala Gly Ser Ser Gly Asn Lys Trp Ala Met Asp Tyr Trp Gly His
            100                 105                 110

Gly Ala Ser Val Thr Val Ser Ser Ser Gly Ser Ser Ser Ser Gly Ser
            115                 120                 125
```

| | | | | | | | | | | | | | | | |
|---|---|---|---|---|---|---|---|---|---|---|---|---|---|---|---|
| Ser | Ser | Ser | Gly | Ser | Asp | Val | Val | Met | Thr | Gln | Thr | Pro | Leu | Ser | Leu |
| | | 130 | | | | 135 | | | | 140 | | | | | |
| Pro | Val | Ser | Leu | Gly | Asp | Gln | Ala | Ser | Ile | Ser | Cys | Arg | Ser | Ser | Gln |
| 145 | | | | | 150 | | | | | 155 | | | | | 160 |
| Ser | Leu | Val | His | Ser | Asn | Gly | Asn | Thr | Tyr | Leu | Asn | Trp | Tyr | Leu | Gln |
| | | | | 165 | | | | | 170 | | | | | 175 | |
| Lys | Ala | Gly | Gln | Ser | Pro | Lys | Leu | Leu | Ile | Tyr | Lys | Val | Ser | Asn | Arg |
| | | | 180 | | | | | 185 | | | | | 190 | | |
| Phe | Ser | Gly | Val | Pro | Asp | Arg | Phe | Ser | Gly | Ser | Gly | Ser | Gly | Thr | Asp |
| | | 195 | | | | | 200 | | | | | 205 | | | |
| Phe | Thr | Leu | Lys | Ile | Ser | Arg | Val | Glu | Ala | Glu | Asp | Leu | Gly | Ile | Tyr |
| | 210 | | | | | 215 | | | | | 220 | | | | |
| Phe | Cys | Ser | Gln | Thr | Thr | His | Val | Pro | Pro | Thr | Phe | Gly | Gly | Gly | Thr |
| 225 | | | | | 230 | | | | | 235 | | | | | 240 |
| Lys | Leu | Glu | Ile | Lys | Arg | | | | | | | | | | |
| | | | | 245 | | | | | | | | | | | |

( 2 ) INFORMATION FOR SEQ ID NO:8:

( i ) SEQUENCE CHARACTERISTICS:
        ( A ) LENGTH: 1415 base pairs
        ( B ) TYPE: nucleic acid
        ( C ) STRANDEDNESS: single
        ( D ) TOPOLOGY: linear ( i i ) MOLECULE TYPE: syn DNA ( i x ) FEATURE:
        ( A ) NAME/KEY: CDS
        ( B ) LOCATION: 1..1415

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| ATG | GTT | CGA | CCA | TTG | AAC | TGC | ATC | GTC | GCC | GTG | TCC | CAA | AAT | ATG | GGG | 48 |
| Met | Val | Arg | Pro | Leu | Asn | Cys | Ile | Val | Ala | Val | Ser | Gln | Asn | Met | Gly | |
| 1 | | | | 5 | | | | | 10 | | | | | 15 | | |
| ATT | GGC | AAG | AAC | GGA | GAC | CGA | CCC | TGG | CCT | CCG | CTC | AGG | AAC | GAG | TTC | 96 |
| Ile | Gly | Lys | Asn | Gly | Asp | Arg | Pro | Trp | Pro | Pro | Leu | Arg | Asn | Glu | Phe | |
| | | | 20 | | | | | 25 | | | | | 30 | | | |
| AAG | TAC | TTC | CAA | AGA | ATG | ACC | ACA | ACC | TCT | TCA | GTG | GAA | GGT | AAA | CAG | 144 |
| Lys | Tyr | Phe | Gln | Arg | Met | Thr | Thr | Thr | Ser | Ser | Val | Glu | Gly | Lys | Gln | |
| | | 35 | | | | | 40 | | | | | 45 | | | | |
| AAT | CTG | GTG | ATT | ATG | GGT | AGG | AAA | ACC | TGG | TTC | TCC | ATT | CCT | GAG | AAG | 192 |
| Asn | Leu | Val | Ile | Met | Gly | Arg | Lys | Thr | Trp | Phe | Ser | Ile | Pro | Glu | Lys | |
| | 50 | | | | | 55 | | | | | 60 | | | | | |
| AAT | CGA | CCT | TTA | AAG | GAC | AGA | ATT | AAT | ATA | GTT | CTC | AGT | AGA | GAA | CTC | 240 |
| Asn | Arg | Pro | Leu | Lys | Asp | Arg | Ile | Asn | Ile | Val | Leu | Ser | Arg | Glu | Leu | |
| 65 | | | | | 70 | | | | | 75 | | | | | 80 | |
| AAA | GAA | CCA | CCA | CGA | GGA | GCT | CAT | TTT | CTT | GCC | AAA | AGT | TTG | GAT | GAT | 288 |
| Lys | Glu | Pro | Pro | Arg | Gly | Ala | His | Phe | Leu | Ala | Lys | Ser | Leu | Asp | Asp | |
| | | | | 85 | | | | | 90 | | | | | 95 | | |
| GCC | TTA | AGA | CTT | ATT | GAA | CAA | CCG | GAA | TTG | GCA | AGT | AAA | GTA | GAC | ATG | 336 |
| Ala | Leu | Arg | Leu | Ile | Glu | Gln | Pro | Glu | Leu | Ala | Ser | Lys | Val | Asp | Met | |
| | | | 100 | | | | | 105 | | | | | 110 | | | |
| GTT | TGG | ATA | GTC | GGA | GGC | AGT | TCT | GTT | TAC | CAG | GAA | GCC | ATG | AAT | CAA | 384 |
| Val | Trp | Ile | Val | Gly | Gly | Ser | Ser | Val | Tyr | Gln | Glu | Ala | Met | Asn | Gln | |
| | | 115 | | | | | 120 | | | | | 125 | | | | |
| CCA | GGC | CAC | CTC | AGA | CTC | TTT | GTG | ACA | AGG | ATC | ATG | CAG | GAA | TTT | GAA | 432 |
| Pro | Gly | His | Leu | Arg | Leu | Phe | Val | Thr | Arg | Ile | Met | Gln | Glu | Phe | Glu | |
| | | 130 | | | | | 135 | | | | | 140 | | | | |
| AGT | GAC | ACG | TTT | TTC | CCA | GAA | ATT | GAT | TTG | GGG | AAA | TAT | AAA | CTT | CTC | 480 |
| Ser | Asp | Thr | Phe | Phe | Pro | Glu | Ile | Asp | Leu | Gly | Lys | Tyr | Lys | Leu | Leu | |

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
| 145 |     |     |     |     | 150 |     |     |     |     | 155 |     |     |     |     | 160 |     |
| CCA | GAA | TAC | CCA | GGC | GTC | CTC | TCT | GAG | GTC | CAG | GAG | GAA | AAA | GGC | ATC | 528 |
| Pro | Glu | Tyr | Pro | Gly<br>165 | Val | Leu | Ser | Glu | Val<br>170 | Gln | Glu | Glu | Lys | Gly<br>175 | Ile |     |
| AAG | TAT | AAG | TTT | GAA | GTC | TAC | GAG | AAG | AAA | GAC | GCT | AGC | GTT | ACT | GTG | 576 |
| Lys | Tyr | Lys | Phe<br>180 | Glu | Val | Tyr | Glu | Lys | Lys<br>185 | Asp | Ala | Ser | Val | Thr<br>190 | Val |     |
| AGC | TCC | TCC | GGA | TCT | TCA | TCT | AGC | GGT | TCC | AGC | TCG | AGT | GGA | TCT | ATG | 624 |
| Ser | Ser | Ser<br>195 | Gly | Ser | Ser | Ser | Ser | Gly<br>200 | Ser | Ser | Ser | Ser | Gly<br>205 | Ser | Met |     |
| ATT | GAA | CAA | GAT | GGA | TTG | CAC | GCA | GGT | TCT | CCG | GCC | GCT | TGG | GTG | GAG | 672 |
| Ile | Glu | Gln<br>210 | Asp | Gly | Leu | His<br>215 | Ala | Gly | Ser | Pro | Ala<br>220 | Ala | Trp | Val | Glu |     |
| AGG | CTA | TTC | GGC | TAT | GAC | TGG | GCA | CAA | CAG | ACA | ATC | GGC | TGC | TCT | GAT | 720 |
| Arg<br>225 | Leu | Phe | Gly | Tyr | Asp<br>230 | Trp | Ala | Gln | Gln | Thr<br>235 | Ile | Gly | Cys | Ser | Asp<br>240 |     |
| GCC | GCC | GTG | TTC | CGG | CTG | TCA | GCG | CAG | GGG | CGC | CCG | GTT | CTT | TTT | GTC | 768 |
| Ala | Ala | Val | Phe | Arg<br>245 | Leu | Ser | Ala | Gln | Gly<br>250 | Arg | Pro | Val | Leu | Phe<br>255 | Val |     |
| AAG | ACC | GAC | CTG | TCC | GGT | GCC | CTG | AAT | GAA | CTG | CAG | GAC | GAG | GCA | GCG | 816 |
| Lys | Thr | Asp | Leu<br>260 | Ser | Gly | Ala | Leu | Asn<br>265 | Glu | Leu | Gln | Asp | Glu<br>270 | Ala | Ala |     |
| CGG | CTA | TCG | TGG | CTG | GCC | ACG | ACG | GGC | GTT | CCT | TGC | GCA | GCT | GTG | CTC | 864 |
| Arg | Leu | Ser<br>275 | Trp | Leu | Ala | Thr | Thr<br>280 | Gly | Val | Pro | Cys | Ala<br>285 | Ala | Val | Leu |     |
| GAC | GTT | GTC | ACT | GAA | GCG | GGA | AGG | GAC | TGG | CTG | CTA | TTG | GGC | GAA | GTG | 912 |
| Asp | Val | Val<br>290 | Thr | Glu | Ala | Gly | Arg<br>295 | Asp | Trp | Leu | Leu | Leu<br>300 | Gly | Glu | Val |     |
| CCG | GGG | CAG | GAT | CTC | CTG | TCA | TCT | CAC | CTT | GCT | CCT | GCC | GAG | AAA | GTA | 960 |
| Pro<br>305 | Gly | Gln | Asp | Leu | Leu<br>310 | Ser | Ser | His | Leu | Ala<br>315 | Pro | Ala | Glu | Lys | Val<br>320 |     |
| TCC | ATC | ATG | GCT | GAT | GCA | ATG | CGG | CGG | CTG | CAT | ACG | CTT | GAT | CCG | GCT | 1008 |
| Ser | Ile | Met | Ala | Asp<br>325 | Ala | Met | Arg | Arg | Leu<br>330 | His | Thr | Leu | Asp | Pro<br>335 | Ala |     |
| ACC | TGC | CCA | TTC | GAC | CAC | CAA | GCG | AAA | CAT | CGC | ATC | GAG | CGA | GCA | CGT | 1056 |
| Thr | Cys | Pro | Phe<br>340 | Asp | His | Gln | Ala | Lys<br>345 | His | Arg | Ile | Glu | Arg<br>350 | Ala | Arg |     |
| ACT | CGG | ATG | GAA | GCC | GGT | CTT | GTC | GAT | CAG | GAT | GAT | CTG | GAC | GAA | GAG | 1104 |
| Thr | Arg | Met<br>355 | Glu | Ala | Gly | Leu | Val<br>360 | Asp | Gln | Asp | Asp | Leu<br>365 | Asp | Glu | Glu |     |
| CAT | CAG | GGG | CTC | GCG | CCA | GCC | GAA | CTG | TTC | GCC | AGG | CTC | AAG | GCG | CGC | 1152 |
| His | Gln<br>370 | Gly | Leu | Ala | Pro | Ala<br>375 | Glu | Leu | Phe | Ala | Arg<br>380 | Leu | Lys | Ala | Arg |     |
| ATG | CCC | GAC | GGC | GAG | GAT | CTC | GTC | GTG | ACC | CAT | GGC | GAT | GCC | TGC | TTG | 1200 |
| Met<br>385 | Pro | Asp | Gly | Glu | Asp<br>390 | Leu | Val | Val | Thr | His<br>395 | Gly | Asp | Ala | Cys | Leu<br>400 |     |
| CCG | AAT | ATC | ATG | GTG | GAA | AAT | GGC | CGC | TTT | TCT | GGA | TTC | ATC | GAC | TGT | 1248 |
| Pro | Asn | Ile | Met | Val<br>405 | Glu | Asn | Gly | Arg | Phe<br>410 | Ser | Gly | Phe | Ile | Asp<br>415 | Cys |     |
| GGC | CGG | CTG | GGT | GTG | GCG | GAC | CGC | TAT | CAG | GAC | ATA | GCG | TTG | GCT | ACC | 1296 |
| Gly | Arg | Leu | Gly<br>420 | Val | Ala | Asp | Arg | Tyr<br>425 | Gln | Asp | Ile | Ala | Leu<br>430 | Ala | Thr |     |
| CGT | GAT | ATT | GCT | GAA | GAG | CTT | GGC | GGC | GAA | TGG | GCT | GAC | CGC | TTC | CTC | 1344 |
| Arg | Asp | Ile<br>435 | Ala | Glu | Glu | Leu | Gly<br>440 | Gly | Glu | Trp | Ala | Asp<br>445 | Arg | Phe | Leu |     |
| GTG | CTT | TAC | GGT | ATC | GCC | GCT | CCC | GAT | TCG | CAG | CGC | ATC | GCC | TTC | TAT | 1392 |
| Val | Leu | Tyr<br>450 | Gly | Ile | Ala | Ala | Pro<br>455 | Asp | Ser | Gln | Arg | Ile<br>460 | Ala | Phe | Tyr |     |
| CGC | CTT | CTT | GAC | GAG | TTC | TTC | TG |     |     |     |     |     |     |     |     | 1415 |
| Arg | Leu | Leu | Asp | Glu | Phe | Phe |     |     |     |     |     |     |     |     |     |     |

( 2 ) INFORMATION FOR SEQ ID NO:9:

( i ) SEQUENCE CHARACTERISTICS:
        ( A ) LENGTH: 471 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Val Arg Pro Leu Asn Cys Ile Val Ala Val Ser Gln Asn Met Gly
 1               5                  10                  15

Ile Gly Lys Asn Gly Asp Arg Pro Trp Pro Pro Leu Arg Asn Glu Phe
                20                  25                  30

Lys Tyr Phe Gln Arg Met Thr Thr Thr Ser Ser Val Glu Gly Lys Gln
             35                  40                  45

Asn Leu Val Ile Met Gly Arg Lys Thr Trp Phe Ser Ile Pro Glu Lys
         50                  55                  60

Asn Arg Pro Leu Lys Asp Arg Ile Asn Ile Val Leu Ser Arg Glu Leu
 65                  70                  75                  80

Lys Glu Pro Pro Arg Gly Ala His Phe Leu Ala Lys Ser Leu Asp Asp
                 85                  90                  95

Ala Leu Arg Leu Ile Glu Gln Pro Glu Leu Ala Ser Lys Val Asp Met
             100                 105                 110

Val Trp Ile Val Gly Gly Ser Ser Val Tyr Gln Glu Ala Met Asn Gln
         115                 120                 125

Pro Gly His Leu Arg Leu Phe Val Thr Arg Ile Met Gln Glu Phe Glu
130                 135                 140

Ser Asp Thr Phe Phe Pro Glu Ile Asp Leu Gly Lys Tyr Lys Leu Leu
145                 150                 155                 160

Pro Glu Tyr Pro Gly Val Leu Ser Glu Val Gln Glu Glu Lys Gly Ile
                165                 170                 175

Lys Tyr Lys Phe Glu Val Tyr Glu Lys Lys Asp Ala Ser Val Thr Val
            180                 185                 190

Ser Ser Ser Gly Ser Ser Ser Gly Ser Ser Ser Ser Gly Ser Ser Met
        195                 200                 205

Ile Glu Gln Asp Gly Leu His Ala Gly Ser Pro Ala Ala Trp Val Glu
    210                 215                 220

Arg Leu Phe Gly Tyr Asp Trp Ala Gln Gln Thr Ile Gly Cys Ser Asp
225                 230                 235                 240

Ala Ala Val Phe Arg Leu Ser Ala Gln Gly Arg Pro Val Leu Phe Val
                245                 250                 255

Lys Thr Asp Leu Ser Gly Ala Leu Asn Glu Leu Gln Asp Glu Ala Ala
            260                 265                 270

Arg Leu Ser Trp Leu Ala Thr Thr Gly Val Pro Cys Ala Ala Val Leu
        275                 280                 285

Asp Val Val Thr Glu Ala Gly Arg Asp Trp Leu Leu Leu Gly Glu Val
    290                 295                 300

Pro Gly Gln Asp Leu Leu Ser Ser His Leu Ala Pro Ala Glu Lys Val
305                 310                 315                 320

Ser Ile Met Ala Asp Ala Met Arg Arg Leu His Thr Leu Asp Pro Ala
                325                 330                 335

Thr Cys Pro Phe Asp His Gln Ala Lys His Arg Ile Glu Arg Ala Arg
            340                 345                 350
```

| | | | | | | | | | | | | | | |
|---|---|---|---|---|---|---|---|---|---|---|---|---|---|---|
| Thr | Arg | Met 355 | Glu | Ala | Gly | Leu | Val 360 | Asp | Gln | Asp | Asp | Leu 365 | Asp | Glu | Glu |
| His | Gln 370 | Gly | Leu | Ala | Pro | Ala 375 | Glu | Leu | Phe | Ala | Arg 380 | Leu | Lys | Ala | Arg |
| Met 385 | Pro | Asp | Gly | Glu | Asp 390 | Leu | Val | Val | Thr | His 395 | Gly | Asp | Ala | Cys | Leu 400 |
| Pro | Asn | Ile | Met | Val 405 | Glu | Asn | Gly | Arg | Phe 410 | Ser | Gly | Phe | Ile | Asp 415 | Cys |
| Gly | Arg | Leu | Gly 420 | Val | Ala | Asp | Arg | Tyr 425 | Gln | Asp | Ile | Ala | Leu 430 | Ala | Thr |
| Arg | Asp | Ile 435 | Ala | Glu | Glu | Leu | Gly 440 | Gly | Glu | Trp | Ala | Asp 445 | Arg | Phe | Leu |
| Val | Leu 450 | Tyr | Gly | Ile | Ala | Ala 455 | Pro | Asp | Ser | Gln | Arg 460 | Ile | Ala | Phe | Tyr |
| Arg 465 | Leu | Leu | Asp | Glu | Phe 470 | Phe | | | | | | | | | |

What is claimed is:

1. An isolated chimeric protein construct comprising first and second protein domains biologically active individually or together, said domains being connected by a peptide linker comprising the sequence (Ser-Ser-Ser-Ser-Gly)$_y$, wherein y is at least 1.

2. An isolated chimeric protein construct comprising first and second protein domains biologically active individually or together, said domains being connected by a peptide linker comprising between 8 and 30 amino acid residues, at least 60% of the residues being Ser.

3. The isolated chimeric protein construct of claim 1 or 2 wherein one of said protein domains comprises an antibody heavy chain variable region (VH) and the other of said protein domains comprises an antibody light chain variable region (VL).

4. The isolated chimeric protein construct of claim 3 labeled with a radioactive isotope.

5. The isolated chimeric protein construct of claim 1 or 2 wherein the first domain comprises a polypeptide ligand and the second domain comprises a polypeptide effector, said ligand being capable of binding to a receptor or adhesion molecule on a cell and said effector being capable of affecting the metabolism of the cell.

6. The isolated chimeric protein construct of claim 5, wherein the ligand is an antibody fragment.

7. The isolated chimeric protein construct of claim 5, wherein the effector is a toxin.

8. The isolated chimeric protein construct of claim 1, wherein y is any integer selected to optimize the biological function and three dimensional conformation of the chimeric protein construct.

9. The isolated chimeric protein construct of claim 1 wherein said linker comprises the sequence set forth in SEQ. ID No. 1.

10. The isolated chimeric protein construct of claim 1 wherein y is an integer between 1 and 5.

11. A method for producing an isolated chimeric protein construct, comprising:

transforming a cell with a DNA encoding the chimeric protein construct of claim 1 or 2;

inducing the transformed cell to express said chimeric protein construct; and collecting said expressed chimeric protein construct.

12. A DNA encoding the chimeric protein construct of claim 1 or 2.

13. A cell which expresses the DNA of claim 12.

14. An isolated chimeric protein construct comprising two domains one having the structure of an antibody light chain variable region (VL) and the other having the structure of an antibody heavy chain variable region (VH), joined by a peptide linker, wherein said linker comprises between 8 and 30 amino acid residues, at least 60% of the residues being serine.

15. The isolated chimeric protein construct of claim 2 or 14 wherein the linker is free of charged amino acid residues.

16. The isolated chimeric protein construct of claim 2 or 14 wherein the linker consists of serine and glycine amino acid residues.

17. The isolated chimeric protein construct of claim 2 or 14 wherein the linker comprises at least 80% serine residues.

18. The isolated chimeric protein construct of claim 2 or 14 wherein the linker comprises the following amino acid sequence set forth in SEO. ID No. 1:

Ser-Gly-Ser-Ser-Ser-Ser-Gly-Ser-Ser-Ser-Ser-Gly-Ser

19. The isolated chimeric protein construct of claim 1, 2, or 14 wherein the linker is soluble at physiologically acceptable pH and ionic strength.

* * * * *